(12) United States Patent
Guo et al.

(10) Patent No.: US 9,481,839 B2
(45) Date of Patent: Nov. 1, 2016

(54) HOT OXYGEN NOZZLE AND USES THEREOF IN GASIFIERS

(71) Applicant: EAST CHINA UNIVERSITY OF SCIENCE AND TECHNOLOGY, Shanghai (CN)

(72) Inventors: Qinghua Guo, Shanghai (CN); Tao Wang, Shanghai (CN); Zhenghua Dai, Shanghai (CN); Guangsuo Yu, Shanghai (CN); Xin Gong, Shanghai (CN); Fuchen Wang, Shanghai (CN); Haifeng Liu, Shanghai (CN); Yifei Wang, Shanghai (CN); William J. Mahoney, East Aurora, NY (US); Sabuj Halder, Kristiansand (NO); Yi Ma, Tomball, TX (US); Jie Zhang, Shanghai (CN); Zhijie Zhou, Shanghai (CN); Robert J. Churpita, Tonawanda, NY (US); Christopher Herby, Buffalo, NY (US); William Jeffrey Wilson, Wheatfield, NY (US); Zhuoyong Yan, Shanghai (CN)

(73) Assignees: PRAXAIR TECHNOLOGY, INC., Danbury, CT (US); EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 14/421,042

(22) PCT Filed: Nov. 26, 2013

(86) PCT No.: PCT/CN2013/001443
§ 371 (c)(1),
(2) Date: Feb. 11, 2015

(87) PCT Pub. No.: WO2014/082373
PCT Pub. Date: Jun. 5, 2014

(65) Prior Publication Data
US 2015/0218470 A1 Aug. 6, 2015

(30) Foreign Application Priority Data

Nov. 28, 2012 (CN) .......................... 2012 1 0493142

(51) Int. Cl.
*F23L 7/00* (2006.01)
*F23N 5/00* (2006.01)
(Continued)

(52) U.S. Cl.
CPC .................. *C10J 3/80* (2013.01); *B05B 1/005* (2013.01); *C01B 3/02* (2013.01); *C01B 3/363* (2013.01);
(Continued)

(58) Field of Classification Search
CPC ......... F23N 1/002; C10J 3/503; C10J 3/506; C10J 3/723; C10J 3/74; C10J 3/76; F23R 3/36; F23R 3/28; F23D 17/00
USPC ............. 431/75, 187, 233, 354; 60/740, 781
See application file for complete search history.

(56) References Cited

U.S. PATENT DOCUMENTS

| | | | | |
|---|---|---|---|---|
| 4,443,228 A * | 4/1984 | Schlinger | ................ | C01B 3/363 239/112 |
| 4,443,230 A * | 4/1984 | Stellaccio | ................ | C10J 3/506 252/373 |

(Continued)

FOREIGN PATENT DOCUMENTS

| CN | 2306406 Y | * | 2/1999 | ............... F23N 3/00 |
|---|---|---|---|---|
| CN | 1752521 A | | 3/2006 | |

(Continued)

*Primary Examiner* — William G Corboy
(74) *Attorney, Agent, or Firm* — Donald T. Black

(57) ABSTRACT

A hot oxygen nozzle and uses thereof in a gasifier, the hot oxygen nozzle comprising an outer-ring spout, a middle-ring spout, an inner-ring spout, and a central spout all sequentially and coaxially disposed, and a cooling system; the gasifier is an entrained-flow gasifier provided with one or more nozzles on a certain plane or a plurality of planes at the top or on the periphery of the gasifier body. The nozzle has a simple structure and is easy to make and maintain. A fuel gas passage is disposed inside the nozzle. Oxygen can be heated by a combustion of fuel gas; and high-temperature and high-speed oxygen can directly ignite carbonaceous materials such as coal-water slurry and coke-oven gas. The present invention can be applied in a gasifier and then in the final process of synthesis gas preparation.

4 Claims, 2 Drawing Sheets

(51) Int. Cl.
- F23C 7/00 (2006.01)
- F23D 11/44 (2006.01)
- C10J 3/80 (2006.01)
- C10J 3/76 (2006.01)
- F23R 3/36 (2006.01)
- C10J 3/74 (2006.01)
- F23D 17/00 (2006.01)
- C10J 3/72 (2006.01)
- F23R 3/28 (2006.01)
- F23N 1/00 (2006.01)
- C10J 3/50 (2006.01)
- F23D 14/22 (2006.01)
- F23D 14/32 (2006.01)
- F23D 14/52 (2006.01)
- F23D 14/78 (2006.01)
- B05B 1/00 (2006.01)
- C01B 3/02 (2006.01)
- C01C 1/02 (2006.01)
- C07C 29/04 (2006.01)
- F01K 23/10 (2006.01)
- F02C 3/28 (2006.01)
- F23D 14/66 (2006.01)
- C01B 3/36 (2006.01)

(52) U.S. Cl.
CPC ............... *C01C 1/02* (2013.01); *C07C 29/04* (2013.01); *C10J 3/506* (2013.01); *C10J 3/723* (2013.01); *C10J 3/74* (2013.01); *C10J 3/76* (2013.01); *F01K 23/10* (2013.01); *F02C 3/28* (2013.01); *F23D 14/22* (2013.01); *F23D 14/32* (2013.01); *F23D 14/52* (2013.01); *F23D 14/66* (2013.01); *F23D 14/78* (2013.01); *F23D 17/00* (2013.01); *F23N 1/002* (2013.01); *F23R 3/28* (2013.01); *F23R 3/36* (2013.01); *C01B 2203/0255* (2013.01); *C01B 2203/061* (2013.01); *C01B 2203/068* (2013.01); *C01B 2203/84* (2013.01); *C10J 2200/152* (2013.01); *C10J 2300/093* (2013.01); *C10J 2300/0946* (2013.01); *C10J 2300/0959* (2013.01); *C10J 2300/0973* (2013.01); *C10J 2300/1253* (2013.01); *C10J 2300/1665* (2013.01); *C10J 2300/1668* (2013.01); *C10J 2300/1675* (2013.01); *C10J 2300/1846* (2013.01); *F05D 2220/32* (2013.01); *F05D 2220/722* (2013.01); *Y02E 20/18* (2013.01); *Y02E 20/344* (2013.01)

(56) References Cited

U.S. PATENT DOCUMENTS

| | | |
|---|---|---|
| 8,105,074 B2 | 1/2012 | Mahoney et al. |
| 2007/0095046 A1* | 5/2007 | Wallace ............ B01J 4/001 60/39.12 |

FOREIGN PATENT DOCUMENTS

| | | |
|---|---|---|
| CN | 102268300 A | 12/2011 |
| CN | 102408919 A | 4/2012 |
| CN | 102492477 A | 6/2012 |
| CN | 102492479 A | 6/2012 |
| CN | 102977926 A | 3/2013 |
| JP | S5996193 A | 6/1984 |

* cited by examiner

HOT OXYGEN NOZZLE AND USES THEREOF IN GASIFIERS

TECHNICAL FIELD

The present invention belongs to the field of coal gasification, and relates to a novel hot oxygen nozzle, more particularly to its use in the gasification of coal water slurry (CWS) and other carbonaceous materials to produce synthesis gas ($CO+H_2$).

BACKGROUND

In China today, clean and efficient use of coal is a priority for the energy sector and for environmental protection. It is also one of the technological keys to the sustainable growth of China's economy. Gasification is the main way to convert primary energy into clean secondary energy. The products of gasification are fuel gas (coal gas), synthesis gas, reducing agent gas, hydrogen, and carbon monoxide. Coal gasification technologies are widely used in the fields of integrated gasification combined cycle (IGCC) power generation, ammonia and methanol synthesis, manufacture of acetic acid and acetic anhydride by methanol carbonylation, manufacture of sponge iron, preparation of pure carbon monoxide, and preparation of pure hydrogen. As the gasifier is a critical piece of equipment in coal gasification, scientists and researchers have developed numerous types of gasifiers. At present, representative technologies that employ entrained-flow gasification include: GE (Taxaco) gasification technology, which uses CWS as a raw material; Shell gasification technology, which uses dry pulverized coal as a raw material; and opposed multi-burner (OMB) gasification technology, which uses CWS or dry pulverized coal as a raw material.

In a refractory brick-lined gasifier fed by CWS as a raw material, the feeding process requires the use of pre-heating nozzles to heat the gasifier, raise the temperature to >1000° C., and maintain the temperature level. The nozzles are then replaced by processing nozzles in order to feed the gasifier. This is a relatively complex process with high fuel consumption and long startup and shutdown times, and therefore, is not conducive to the continuous and stable operation of chemical production facilities.

The objective of the present invention is to further optimize the structure of the conventional nozzle by disclosing a hot oxygen nozzle and uses thereof in gasifiers, which enable the direct ignition and use of fuel and shorten gasifier heating, startup, and shutdown times. In particular, for a hot wall gasifier in a hot standby state, this nozzle not only operates as reliably as a conventional nozzle, but is also capable of direct ignition and feeding at a lower gasifier temperature. This nozzle has a simple structure and is easy to make and maintain, which makes its wider application worthwhile.

SUMMARY OF THE INVENTION

The present invention relates to a hot oxygen nozzle, which can raise the temperature of oxygen to 500° C. or higher. At a higher oxygen temperature, CWS and other carbonaceous materials can be directly ignited. Based on the characteristics of the nozzle, and in order to simplify the startup and operation of the aforementioned conventional gasification process, the present invention discloses a hot oxygen nozzle structure and uses thereof in gasifiers.

The conception of the invention is as follows: Existing gasification technologies, especially the CWS-based gasification technologies, depending on different types of coals and operating conditions, require an increase of gasifier temperature to approximately 1,200° C., then a replacement by processing nozzles, a nitrogen purge, and feeding. The U.S. Pat. No. 8,105,074B2 discloses a hot oxygen generator, which, by regulating the flow rate and ratio of gasification agents and fuel gas, heats oxygen up to 1500° C. At this temperature, CWS and other carbonaceous fuels can be directly ignited. Thus, a hot oxygen nozzle can significantly reduce fuel consumption in the preheating of gasifiers and further enhance facility safety. Due to the high temperature of the oxygen, its exit velocity is greater than that of room-temperature oxygen. High-speed oxygen jets can enhance the atomization of fuels such as CWS, further increasing the carbon conversion rate of fuels. In addition, high-speed oxygen rapidly transports the heat generated during fuel gas combustion, preventing damage to nozzles by high temperatures.

The technical solution used to achieve the objective of the present invention:

A hot oxygen nozzle comprises an outer-ring spout, a middle-ring spout, an inner-ring spout, and a central spout all sequentially and coaxially disposed, and a cooling system. The outer-ring spout comprises an outer-ring duct and an outer-ring nozzle head. The larger end of the outer-ring nozzle head is connected to the outer-ring duct. The central spout comprises a central duct and a central nozzle head. The larger end of the central nozzle head is connected to the central duct. The middle-ring spout comprises a middle-ring duct. The inner-ring spout comprises an inner-ring duct. The outer-ring spout, middle-ring spout, inner-ring spout, and central spout are connected by a flange. The end of the outer-ring spout is level with that of the central spout.

The cooling system comprises coils and a cooling chamber. The cooling chamber is coaxially situated on the outside of the outer-ring nozzle head. The coils are situated on the outside of the outer-ring duct close to the outer-ring nozzle head. The cooling chamber is connected with the coils. Liquid coolants flow into the cooling chamber and then flow out through the coils.

An outer-ring oxygen passage is formed between the outer-ring spout and the middle-ring spout. An inner-ring oxygen passage is formed between the inner-ring spout and the central spout. A fuel gas passage is formed between the middle-ring spout and the inner-ring spout. A fuel passage is formed within the central spout.

The middle-ring spout and the inner-ring spout subside inward along the axis. The end of the middle-ring spout is level with that of the inner-ring spout. A hot oxygen chamber is formed by the cross-section of the outlet of the fuel gas passage, the inner wall of the straight duct of the outer-ring spout, and the outer wall of the straight duct of the central spout. The length of the hot oxygen chamber, t, is 2-5 times the equivalent diameter of the fuel gas passage.

The inner convergence angle $\alpha$ of the central nozzle head is 45-80°. The outer convergence angle of the central nozzle head equals the inner convergence angle $\beta$ of the outer-ring nozzle head, which is 30-80°.

A gasifier can be provided with any of the hot oxygen nozzles described above. The gasifier can be provided with one or more said hot oxygen nozzles on a certain plane or a plurality of planes at the top or on the periphery of the gasifier body.

The hot oxygen nozzles and the gasifier are connected by a flange.

The gasifier described above is used to prepare synthesis gases from carbonaceous materials, synthesize ammonia and methanol, generate power via IGCC, produce sponge iron, or gasify waste.

The ratio of the flow rate of gasification agents in the outer-ring oxygen passage to that in the inner-ring oxygen passage is: the outer-ring oxygen passage accounts for 50%, the inner-ring oxygen passage accounts for 50%. The ratio of the total amount of gasification agents to the flow rate of fuel gas in the fuel gas passage is 85-97:3-15.

The flow velocities of gasification agents in the outer-ring oxygen passage and in the inner-ring oxygen passage are both 0-50 m/s. The velocity of fuel gas in the fuel gas passage is 0-50 m/s. The flow velocity of carbonaceous materials at the fuel outlet is 0.1-1.0 m/s. The flow velocity of hot gasification agents at the gasification agent outlet is 20-600 m/s.

Fuel gases in the fuel gas passage are an assortment of natural gas, methane, propane, synthesis gas, coke oven gas, or exhaust gas.

The hot oxygen nozzle of the present invention can ignite CWS and other carbonaceous fuels at a low temperature. High-speed, high-temperature oxygen jets not only reinforce the atomization of the fuels, but also enhance heat and mass transfer and chemical reaction rates. In practice, one only needs to ignite a fuel gas at a low flow rate, regulate the gas ratio, control the hot oxygen exit velocity and flow rate, and achieve the ignition of CWS and other carbonaceous fuels. The present invention has an excellent atomization performance, a high carbon conversion rate, a wide scope of applicability, and expansive prospects for application.

Figure 1:
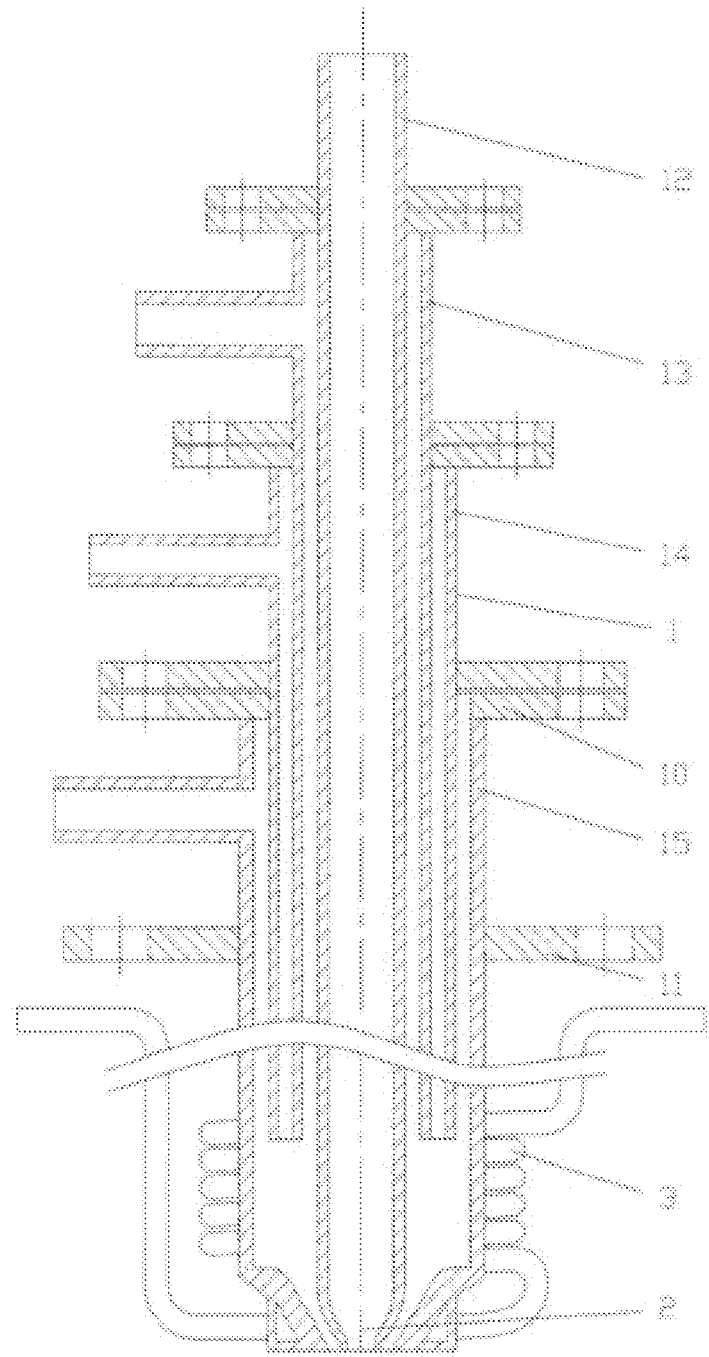
FIG. 1 is a cross-sectional view of the body structure of the hot oxygen nozzle of the invention.

REFERENCE NUMERAL LIST 1 hot oxygen nozzle; 2 nozzle head; 3 coils; 10, 11 flanges; 12 central duct;
13 inner-ring duct; 14 middle-ring duct; 15 outer-ring duct; 16 fuel passage;
17 inner-ring oxygen passage; 18 fuel gas passage; 19 outer-ring oxygen passage;
20 fuel gas outlet; 21 hot oxygen chamber; 22 gasification agent outlet; 23 central nozzle head;
24 fuel outlet; 25 outer-ring nozzle head; 26 cooling chamber.

DETAILED DESCRIPTION OF THE EMBODIMENT

The embodiment below serves to further illustrate the present invention. However, the scope of the present invention is not limited to the embodiment. Variations and modifications made by one skilled in the art without departing from the spirit and scope of the invention are still included within the scope of the present invention.

Figure 2:
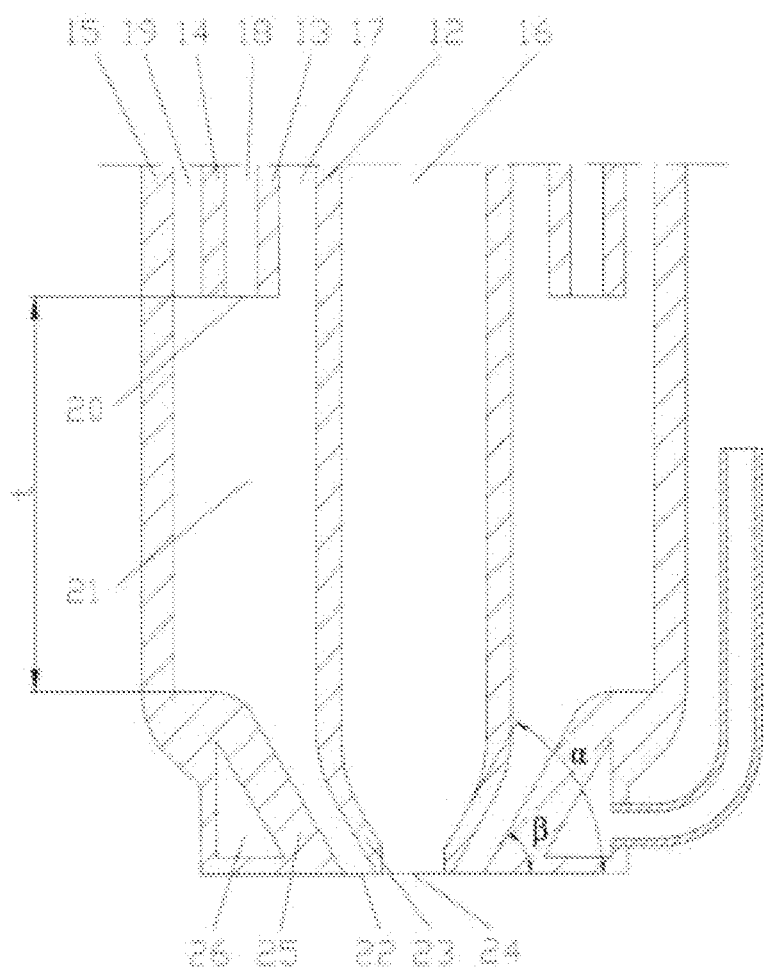
FIG. 2 is a cross-sectional view of the head structure of the hot oxygen nozzle of the invention.

FIG. 1 is a cross-sectional view of the body structure of the hot oxygen nozzle of the invention. FIG. 2 is a cross-sectional view of the head structure of the hot oxygen nozzle of the invention. A hot oxygen nozzle comprises an outer-ring spout, a middle-ring spout, an inner-ring spout, and a central spout all sequentially and coaxially disposed, and a cooling system. The outer-ring spout comprises an outer-ring duct 15 and an outer-ring nozzle head 25. The larger end of the outer-ring nozzle head 25 is connected to the outer-ring duct 15. The central spout comprises a central duct 12 and a central nozzle head 23. The larger end of the central nozzle head 23 is connected to the central duct 12. The middle-ring spout comprises a middle-ring duct 14. The inner-ring spout comprises an inner-ring duct 13. The outer-ring spout, middle-ring spout, inner-ring spout, and central spout are connected by a flange 10. The end of the outer-ring spout is level with that of the central spout.

The cooling system comprises coils 3 and a cooling chamber 26. The cooling chamber 26 is coaxially situated on the outside of the outer-ring nozzle head 25. The coils 3 are situated on the outside of the outer-ring duct 15 close to the outer-ring nozzle head 25. Liquid coolants flow into the cooling chamber 26 and then flow out through the coils 3.

An outer-ring oxygen passage 19 is formed between the outer-ring spout and the middle-ring spout. An inner-ring oxygen passage 17 is formed between the inner-ring spout and the central spout. A fuel gas passage 18 is formed between the middle-ring spout and the inner-ring spout. A fuel passage 16 is formed within the central spout.

The middle-ring spout and the inner-ring spout subside inward along the axis. The end of the middle-ring spout is level with that of the inner-ring spout. A hot oxygen chamber 21 is formed by the cross-section of the outlet 20 of the fuel gas passage 18, the inner wall of the straight duct of the outer-ring spout, and the outer wall of the straight duct of the central spout. The length of the hot oxygen chamber 21, t, is 2-5 times the equivalent diameter of the fuel gas passage 18.

The inner convergence angle $\alpha$ of the central nozzle head 23 is 45-80°. The outer convergence angle of the central nozzle head equals the inner convergence angle $\beta$ of the outer-ring nozzle head, which is 30-80°.

The hot oxygen nozzle described above is connected to a gasifier by a flange 11. The gasifier is provided with one or more hot oxygen nozzles on a certain plane or a plurality of planes at the top or on the periphery of the gasifier body.

A gasifier provided with the hot oxygen nozzle described above can be used for these purposes: preparation of synthesis gases from carbonaceous materials, synthesis of ammonia and methanol, IGCC power generation, production of sponge iron, and waste gasification. Parameters of these applications can be set as follows:

A carbonaceous material with a solids content of 58-80% (wt %) is used as a fuel, with 99.6% oxygen as a gasification agent, and 99% methane as a fuel gas. The gasification agent enters the hot oxygen nozzle through the outer-ring oxygen passage 19 and the inner-ring oxygen passage 17. The fuel enters the hot oxygen nozzle through the fuel passage 16. The fuel gas enters the hot oxygen nozzle through the fuel gas passage 18.

When there is an overall stoichiometric excess of oxygen relative to the oxygen required for complete combustion of the fuel gas in the fuel gas passage 18, the excess oxygen is heated in the hot oxygen chamber 21 and flows out of the gasification agent outlet 22 as a hot gasification agent.

High-temperature, high-speed hot oxygen is mixed and atomized with the fuel at the nozzle exit, enters the gasifier, and results in partial combustion and gasification reactions at the exit.

The ratio of the flow rate of gasification agents to the flow rate of fuel gas in the fuel gas passage is fuel gas: gasification agent=8%.

The ratio of the flow rate of gasification agents in the outer-ring oxygen passage to that in the inner-ring oxygen passage is: the outer-ring oxygen passage accounts for 50%, the inner-ring oxygen passage accounts for 50%. The ratio of the total amount of gasification agents to the flow rate of fuel gas in the fuel gas passage is 85-97:3-15.

The flow velocities of gasification agents in the outer-ring oxygen passage and in the inner-ring oxygen passage are both 0-50 m/s and can be 30 m/s. The velocity of the fuel gas in the fuel gas passage is 0-50 m/s and can be 20 m/s. The flow velocity of carbonaceous materials at the fuel outlet is 0.1-1.0 m/s and can be 0.3 m/s. The flow velocity of hot gasification agents at the gasification agent outlet is 20-600 m/s and can be approximately 300 m/s.

Employing the process described above, the present invention enables the ignition of CWS and other carbonaceous fuels at a lower gasifier temperature. High-temperature oxygen jet flames significantly accelerate heat and mass transfer, thus increasing the carbon conversion rate of fuels.

An example of a gasifier provided with the hot oxygen nozzle described above is as follows:

The hot oxygen nozzle is mounted to the top of a vertical gasifier. CWS with a solids content of 61% is used as a fuel, with 99.8% oxygen as a gasification agent, and 99% methane as a fuel gas. The flow rate of the CWS is 10 kg/h. Fuel gas: gasification agent=8%. Oxygen consumption is 5.6 $Nm^3/h$. Gasification pressure is at atmospheric pressure. Refractory bricks are used as the refractory lining. Gasification temperature is approximately 1,300° C. The height of the gasification chamber is 2.2 m. The interior diameter of the gasification chamber is 0.3 m. The results of the experiment show that the hot oxygen produced at the nozzle can directly ignite the CWS. The flame produced had a uniform and stable shape. At the same temperature, the carbon conversion rate is 2 percentage points higher than that of a normal temperature oxygen nozzle.

The invention claimed is:

1. A hot oxygen nozzle, comprising an outer-ring spout, a middle-ring spout, an inner-ring spout, and a central spout all sequentially and coaxially disposed, and a cooling system, wherein the outer-ring spout has an end and comprises an outer-ring duct and an outer-ring nozzle head which has a larger end; wherein the larger end of the outer-ring nozzle head is connected to the outer-ring duct; wherein the central spout has an end and comprises a central duct and a central nozzle head which has a larger end; wherein the larger end of the central nozzle head is connected to the central duct; wherein the middle-ring spout comprises a middle-ring duct; wherein the inner-ring spout comprises an inner-ring duct; wherein the outer-ring spout, middle-ring spout, inner-ring spout, and central spout are connected by a first flange; wherein the end of the outer-ring spout is level with that of the central spout;

wherein the cooling system comprises coils and a cooling chamber; wherein the cooling chamber is coaxially situated outside of the outer-ring nozzle head; wherein the coils are situated outside of the outer-ring duct close to the outer-ring nozzle head; wherein the cooling chamber is connected with the coils; wherein liquid coolants can flow into the cooling chamber and then can flow out through the coils;

wherein an outer-ring passage is formed between the outer-ring spout and the middle-ring spout; wherein an inner-ring passage is formed between the inner-ring spout and the central spout; wherein a passage is formed between the middle-ring spout and the inner-ring spout; and wherein a passage is formed within the central spout;

wherein the middle-ring spout and the inner-ring spout subside inward along the axis; wherein the end of the middle-ring spout is level with that of the inner-ring spout;

wherein a chamber in which hot oxygen can be created by combustion is formed by the cross-section of the outlet of the passage that is between the middle-ring spout and the inner-ring spout, the inner wall of the straight duct of the outer-ring spout, and the outer wall of the straight duct of the central spout; wherein the length of said chamber, t, as measured from the outlet of the passage that is between the middle-ring spout and the inner-ring spout to an interface between the outer-ring duct and the outer-ring nozzle head is 2-5 times the equivalent diameter of the passage that is between the middle-ring spout and the inner-ring spout;

and wherein the outer-ring passage, the inner-ring passage, and the passage that is between the middle-ring spout and the inner-ring spout, all open into said chamber.

2. A hot oxygen nozzle of claim 1, wherein the central nozzle head has an inner convergence angle $\alpha$ and said inner convergence angle is 45-80°; and wherein the central nozzle head has an outer convergence angle and the outer-ring nozzle head has an inner convergence angle $\beta$ and wherein the outer convergence angle of the central nozzle head equals the inner convergence angle $\beta$ of the outer-ring nozzle head, which is 30-80°.

3. A gasifier provided with the hot oxygen nozzle of claim 1, wherein the gasifier has a top and has a periphery and is provided with one or more of said hot oxygen nozzles on a certain plane or a plurality of planes at the top or on the periphery of the gasifier body.

4. A gasifier of claim 3, wherein the hot oxygen nozzles and the gasifier are connected by a second flange.

* * * * *